United States Patent
Gabbay

Patent Number: 6,149,665
Date of Patent: Nov. 21, 2000

[54] INTRA VASCULAR IMPLANT AND METHOD OF MANUFACTURE THEREOF

[75] Inventor: Shlomo Gabbay, Short Hills, N.J.

[73] Assignee: Shelhigh, Inc., Millburn, N.J.

[21] Appl. No.: 09/355,907

[22] PCT Filed: May 13, 1999

[86] PCT No.: PCT/US99/10505

§ 371 Date: Aug. 5, 1999

§ 102(e) Date: Aug. 5, 1999

[87] PCT Pub. No.: WO99/59502

PCT Pub. Date: Nov. 25, 1999

Related U.S. Application Data

[63] Continuation-in-part of application No. 09/080,042, May 15, 1998, abandoned.

[51] Int. Cl.[7] .................................................. A61M 29/00
[52] U.S. Cl. ............................................................ 606/198
[58] Field of Search .................................. 606/191, 194, 606/195, 198; 623/1, 11, 12

[56] References Cited

U.S. PATENT DOCUMENTS

| | | |
|---|---|---|
| 4,990,131 | 2/1991 | Dardik et al. . |
| 5,380,299 | 1/1995 | Fearnot et al. . |
| 5,645,581 | 7/1997 | Zurbrugg . |

Primary Examiner—Michael Buiz
Assistant Examiner—Vy Q. Bui
Attorney, Agent, or Firm—Amin, Eschweiler & Turocy

[57] ABSTRACT

An implant (10) includes an expandable, flexible membrane (18) mounted over an expandable stent (12), which is releasably affixed to the balloon portion (14) of a catheter (16). The balloon (14) is inflated, thereby enlarging both the stent (12) and the membrane (18). Thereafter, the balloon (14) is deflated and the catheter (16) removed, leaving the stent (12) and membrane (18) in place. The implant (100) may also include an outer stent (106), surrounding a secured membrane (104).

26 Claims, 1 Drawing Sheet

1

INTRA VASCULAR IMPLANT AND METHOD OF MANUFACTURE THEREOF

CROSS REFERENCE TO RELATED APPLICATION

The present application is 371 of PCT/US99/10505 filed May 13, 1999, and a continuation-in-part of U.S. application Ser. No. 09/080,042, which was filed on May 15, 1998, abandoned, and entitled Intra Vascular Implant and Method of Manufacture Thereof.

TECHNICAL FIELD

The present invention is directed to an implant for the circulatory system of a warm blooded animal and a method of manufacture thereof. More specifically, the present invention is directed to an implant for the circulatory system of a warm blooded animal which will minimize or prevent short-term failure and a method of manufacturing such implant.

BACKGROUND OF THE INVENTION

One of the major cardiovascular problems afflicting human beings is the build-up of plague on the inside of blood vessel walls. This narrows the passage for blood and, in more extreme cases, even closes it off entirely.

One of the common treatments is the use of angioplasty. In this method, an inflatable balloon on the end of a catheter is inserted into the blood vessel and inflated at the point of plaque build-up, thereby dilating the artery or vein. However, this procedure provides only temporary relief. The blood vessel tends to return to its original condition within a relatively short period.

To overcome this problem, the procedure has been modified to include the use of a mesh-type metal stent. The stent is crimped around the balloon portion of the catheter and inserted into the blood vessel along with it. The stent has sufficient yieldability so that, when the balloon is inflated, the stent is expanded (see FIG. 1) into contact with the blood vessel walls. The balloon is then deflated and removed, leaving the stent in place. This is a definite improvement over the prior procedure, but is by no means completely satisfactory. In actuality, about 25% to 30% of such stents occlude within six months. This is the result of cellular proliferation whereby the cells grow through the spaces in the grid of the stent, thus developing the blockage anew.

SUMMARY OF THE INVENTION

A first embodiment of the present invention is directed to a method of making an implant for a circulatory system of a warm blooded animal. The method includes surrounding an inert shaft with a flexible membrane. The flexible membrane is contacted with glutaraldehyde to produce a tanned membrane. The flexible membrane is removed from the inert cylinder and placed around an inner expandable stent. Preferably, the stent is releasably attached about a balloon portion of a catheter so that, upon inflation of the balloon portion of the catheter, the stent and membrane are expanded.

Another embodiment of the present invention is directed to an implant for introduction into a circulation system of a warm blooded animal. The implant includes an expandable stent. A flexible membrane, compatible with said warm blooded animal, is mounted about said stent.

Yet another embodiment of the present invention is directed to an implant for introduction into a circulatory system of a warm blooded animal. This embodiment is similar to the implant described above with the addition of an outer stent surrounding the flexible membrane.

BRIEF DESCRIPTION OF THE DRAWINGS

In the accompanying drawings, constituting a part hereof, and in which like reference characters indicate like parts.

DESCRIPTION OF PREFERRED EMBODIMENT

FIGS. 1–4B illustrate the steps for fabricating an implant 10 in accordance with the present invention. The implant 10 advantageously provides the structural reinforcement of conventional stents with the ability to prevent, minimize, or substantially delay the perforation of cells and reformation of blood vessel blockage.

Figure 1:
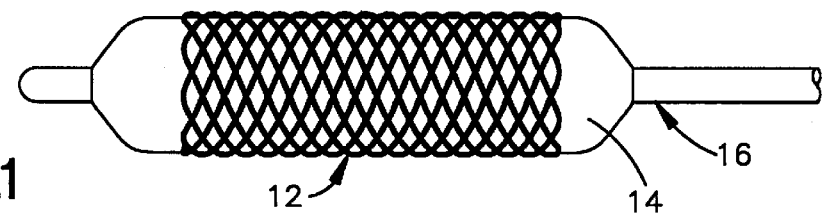
FIG. 1 is side elevation of a stent mounted over a balloon catheter.

FIG. 1 illustrates a stent 12 in an expanded condition mounted over an inflated balloon portion 14 of a catheter 16. Preferably, the stent 12 is in the form of an elongated tube of a foraminous and yieldable material which is capable of radially expanding upon inflation of the balloon portion 14 of the catheter 16. For example, the stent 12 may be formed of stainless steel or another suitable inert metal that is inelastically deformable so that it maintains its shape after being expanded.

The implant 10 also includes a length of a tubular membrane 18 that is inert to the body of a warm blooded animal, e.g., a human being. The membrane 18 is preferably biological tissue, for example, the mammary vein 20 of an animal. The diameter of the membrane 18 is selected to be adequate for the vein or artery being treated.

Figures 2A, 2B, 3:
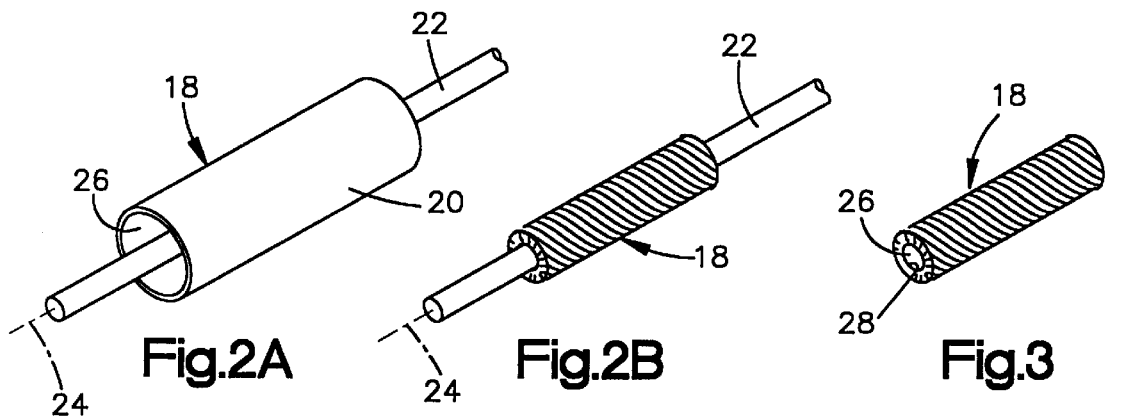
FIG. 2A is a perspective view of a membrane surrounding a wire.
FIG. 2B is a perspective view of the membrane of FIG. 2A after being twisted relative to the wire.
FIG. 3 is a view,,similar to that of FIG. 2B, after the wire has been removed.

The membrane is harvested, cleaned, and stripped down to a sidewall thickness of approximately 0.1 mm. Thereafter, the membrane 18 is placed around a length of a rod or wire 22 and one end of the membrane is secured relative to the wire, such as by a clip or suture (not shown). The free portion of the membrane 18 is then twisted about a longitudinal axis 24 of the wire 22 until the inner diameter of the membrane has been reduced. Preferably, the membrane is twisted relative to the axis 24 sufficiently so that an inner surface 26 of the membrane contacts the wire 22 (FIG. 2B). The other end of the membrane 18 is then secured to the wire 22 to hold the membrane in its twisted configuration.

Since blood vessels to be treated vary in size, the stent 12, membrane 18, and wire 22 are selected accordingly. For example, if a coronary artery is concerned, then the membrane 18 has an original diameter of about 3 to 5 mm. At the same time, the wire is about 0.4 to 0.6 mm. After the membrane 18 has been placed over the wire 22 and twisted, as indicated above, the inner diameter of the membrane corresponds to the outer diameter of the wire, i.e. about 0.4 to 0.6 mm. For larger arteries, the elements are correspondingly increased in size.

The combination of the wire 22 and the membrane 18 are immersed in a glutaraldehyde solution, thereby tanning or fixing the membrane in its twisted configuration. The tanning is substantially complete in about twenty-four hours. Upon completion of the tanning process, the membrane 18 is released and the wire 22 is removed, shown in FIG. 3. The membrane 18 is left in the form of a tube, having an inner diameter approximately that of the outer diameter of the wire 22. The inner surface 26 of the membrane 18 defines a lumen 28 extending longitudinally the length of the membrane. The membrane 18 advantageously maintains its twisted configuration due to the tanning process, although it remains sufficiently flexible so as to facilitate its radial expansion.

Figures 4A, 4B:
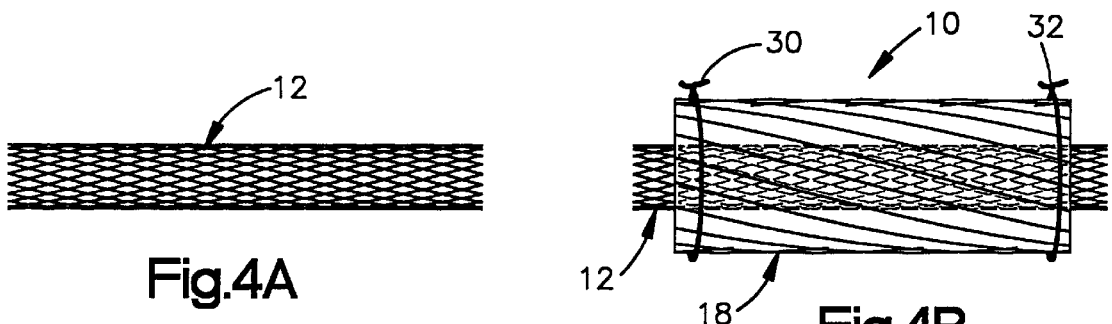
FIG. 4A is a side elevation of a stent.
FIG. 4B is side elevation of an implant in accordance with the present invention.

A greater length of the twisted membrane 18 may be formed as stated above so that it may be used to create a plurality of implants in accordance with the present invention. That is, the tanned length of the twisted membrane 18 is cut into desired lengths for mounting over a corresponding length of the stent 12. The stent 12 is provided with an outer diameter of, for example, about 1 mm. The outer diameter of the stent 12 may be further reduced to a diameter of about 0.8 mm by crimping it, such as with a pair of pliers or with an individual's fingers. The tanned, twisted length of the membrane 18, such as shown in FIG. 3, is placed around the stent 12 of FIG. 4A. Preferably, the twisted length of membrane 18 is selected to be somewhat shorter in length than the stent 12 and positioned axially relative to the stent so that the ends of the stent extend beyond the ends of the membrane, as shown in FIG. 4B.

Because the introduction of almost any foreign body into a blood vessel has a tendency to collect unwanted substances from the bloodstream, the stent 12 and the membrane 18 are bonded with heparin. This reduces the likelihood blood clots being formed. The timing of this step is not critical, it need only be done after tanning with glutaraldehyde and prior to insertion into the patient's body.

The membrane 18 also is secured about the stent 12. For example, one or more sutures 30 and 32 may be tied around the membrane 18 and the stent 12. Desirably, the knots are tied loosely so that, when the balloon 14 is inflated, the knots untie or loosen and allow the membrane 18 and stent 12 to expand. It is also preferable that the sutures 30 and 32 be formed of a material that is absorbable by the body. While a pair of sutures 30 and 32 are illustrated adjacent the ends of the membrane 18, a single suture near the middle also could be used.

Alternatively, the membrane 18 is secured to the stent by configuring the membrane 18 so that the lumen 28 extending through the membrane is smaller than the outer diameter of the stent 12 to be inserted therein. This is accomplished by selecting the wire 22 to have a desired diameter less than the outer diameter of the stent 12. The membrane 18 is flexible and, thus, is able to expand elastically. Accordingly, when the membrane 18 is slid over larger diameter stent 12, the necessary expansion of the membrane causes the stent to grip the membrane firmly. This inhibits relative axial movement between the stent 12 and the membrane 18. This also obviates the need for the sutures 30 and 32, although such sutures still may be used. In addition to dimensioning and configuring the stent 12 as stated above, the outer surface 13 of the stent 12 may be textured or roughened so as to further prevent the membrane 18 from sliding off the stent.

In order to facilitate the attachment of the implant 10 to the balloon portion 14 of the catheter 16, the stent 12 preferably is crimped directly to the balloon portion 14 of the catheter 16. The membrane 18 is then slid over the stent 12 and balloon portion 14 of the catheter 16.

Figure 5:
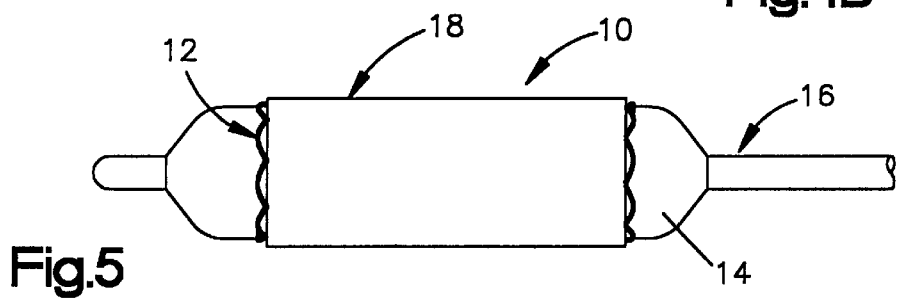
FIG. 5 is a schematic view showing implant of FIG. 4B on a catheter.

In FIG. 5, the membrane 18 and the stent 12 are dilated over the balloon portion 14 of the catheter 16. In practice, the stent 12 and membrane 18 are expanded against the interior wall of a blood vessel being treated. As the implant 10 expands, the twisted sidewall of the membrane 18 untwists, thereby facilitating radial expansion of the implant. After being inflated, the balloon portion 14 is deflated and the catheter 16 is removed. The outer surface of the membrane 18, thus, remains in contact with the blood vessel wall and substantially inhibits cell growth. If the membrane 18 were not configured to be easily expandable, as described herein, the expanded membrane would tend exhibit increased radially inward forces that might collapse the stent 12. As a result, the efficacy of the procedure is greatly enhanced by the implant 10 in accordance with the present invention. When absorbable sutures 30 and 32 are used, they are absorbed by the body over a period of time.

Figure 6:
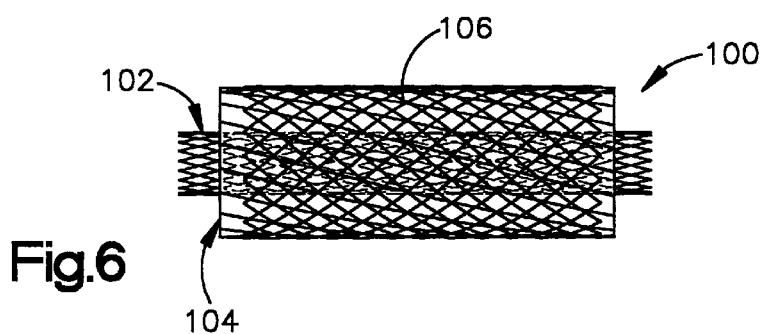
FIG. 6 is a side elevation of an implant in accordance with another embodiment of the present invention.

Another embodiment of an implant 100, in accordance with the present invention, is illustrated in FIG. 6. The implant 100 includes an inner stent 102, which is substantially identical to the stent 10 described with respect to FIGS. 1–5. A length of a tubular sheath or membrane 104 is mounted over the stent 102. Preferably, the membrane 104 is formed of biological tissue, for example the mammary vein of an animal.

The membrane 104 preferably is formed according to a process that is substantially identical to that described with respect to FIGS. 2A, 2B and 3. In particular, the membrane 104 is harvested, cleaned, and stripped to a desirable thickness. A rod or wire is inserted into a lumen formed longitudinally through the membrane 104 and one end of the membrane is affixed relative to the wire. The membrane 104 is twisted relative to the fixed end so that its inner diameter is reduced to that of the wire. The other end is then affixed to the wire to hold the membrane in its twisted configuration and the combination is fixed by a glutaraldehyde solution, as described above. After being fixed, the membrane 104 is released from the wire and the membrane is slid off to form a structure, such as shown in FIG. 3. The membrane 104 is cut to a desirable length for sliding over the stent 102, shown in FIG. 6.

The implant 100 also includes an outer stent 106 formed of an expandable material that is mounted concentrically over the membrane 104 and the inner stent 102. The outer stent 106 is substantially identical to the inner stent 102. Accordingly, the membrane 104 is sandwiched between a pair of inelastically deformable stents 102 and 106.

The implant 100 also is used in a manner as shown and described with respect to FIG. 5. That is, the implant 100 is releasably attached to a balloon portion of a catheter and inserted into the blood vessel to be treated. Once the implant 100 is positioned at the location at which the plaque is deposited or otherwise is in need of reinforcement, the balloon is inflated, thereby causing the inner stent, the membrane 104, and the outer stent 106 to expand radially. The balloon is then deflated and removed, leaving the expanded implant 100 in the blood vessel.

While preferred embodiments of the present invention have been described with respect to a wire onto which the membrane is placed for sizing, any cylindrical object of desired size which is inert to the membrane may be used.

Moreover, any biological tissue may be used in place of the mammary vein, including other veins or tissues from other parts of the animal. Also, synthetic polymers, provided they are—or can be rendered—inert to the body are suitable for this purpose.

From the above description of the invention, those skilled in the art will perceive improvements, changes and modifications. Such improvements, changes and modifications within the skill of the art are intended to be covered by the appended claims.

Having described the invention, the following is claimed:

1. A method of making an implant for a circulatory system of a warm blooded animal, said method comprising steps of:

surrounding at least part of an inert cylinder with a flexible tubular membrane;

twisting said membrane about a longitudinal axis of said inert cylinder, whereby an internal diameter of said membrane is reduced by the step of twisting;

treating said twisted membrane cylinder with glutaraldehyde to produce a tanned membrane;

removing said inert cylinder from said tanned membrane; and placing said tanned membrane around an expandable inner stent.

2. The method of claim 1 further including the step of binding heparin to said tanned membrane to form a bound membrane, said bound membrane being inert to the warm blooded animal.

3. The method of claim 1 further including releasably attaching said inner stent about a balloon portion of a catheter, whereby upon inflation of the balloon portion of the catheter, the stent and membrane are expanded.

4. The method of claim 3 wherein said inner stent is crimped to said balloon portion of said catheter.

5. The method of claim 1 wherein said flexible membrane is a biological tissue.

6. The method of claim 5 wherein said flexible membrane is an animal blood vessel.

7. The method of claim 1 further including the step of securing said membrane to said inner stent to provide a secured membrane.

8. The method of claim 7 wherein said membrane is secured to said inner stent by a suture.

9. The method of claim 8 wherein said suture is absorbable by the warm blooded animal.

10. The method of claim 9 wherein a knot formed in said suture unties as said secured membrane and said inner stent are expanded.

11. The method of claim 8 wherein said step of securing comprises configuring said membrane with an inner diameter smaller than an outer diameter of said inner stent so that said step of placing said membrane around said inner stent causes said membrane to be secured to said inner stent.

12. The method of claim 11 wherein an outer surface of said inner stent is roughened.

13. The method of claim 1 wherein said inert cylinder is a wire.

14. The method of claim 1 wherein said flexible membrane is a polymer inert to said warm blooded animal.

15. The method of claim 1 further comprising the step of placing an outer stent around said bound membrane.

16. An implant for introduction into a circulation system of a warm blooded animal comprising:

an expandable stent;

a tubular membrane, compatible with the warm blooded animal, mounted about said stent, said membrane having a sidewall portion twisted relative to an axis extending longitudinally through said membrane to facilitate radial expansion of said membrane and said stent.

17. The implant of claim 16 wherein said membrane has been tanned with glutaraldehyde to fix said sidewall portion of said membrane in a twisted configuration relative to the axis with an aperture extending longitudinally through said membrane.

18. The implant of claim 17 wherein said tanned membrane has been bound by heparin.

19. The implant of claim 16 wherein said stent is releasably attached around a balloon portion of a catheter, whereby upon inflation of the balloon portion of the catheter the stent-and membrane are expanded radially.

20. The implant of claim 16 wherein said twisted membrane has an inner diameter smaller than an outer diameter of said stent so that, upon mounting said membrane about said stent, said membrane is secured to said stent.

21. The implant of claim 16 wherein said membrane is formed of biological tissue.

22. The implant of claim 21 wherein said biological tissue is a blood vessel from a warm blooded animal.

23. An implant for introduction into a circulatory system of a warm blooded animal comprising:

an inner expandable stent adapted to surround a balloon portion of a catheter;

a membrane surrounding at least a portion of said inner stent and affixed thereto, said membrane having been fixed into an expandable configuration with glutaraldehyde to provide a tanned membrane; and an outer expandable stent surrounding said membrane.

24. The implant of claim 23 wherein said membrane is formed of biological tissue.

25. The implant of claim 23 wherein said membrane has a sidewall portion twisted about an axis extending longitudinally through said membrane to define the expandable configuration fixed by the glutaraldehyde, thereby facilitating radial expansion of said membrane and said inner and outer stents.

26. The implant of claim 23 wherein said tanned membrane has been bound by heparin.

* * * * *